(12) United States Patent
Delury et al.

(10) Patent No.: US 11,877,910 B2
(45) Date of Patent: Jan. 23, 2024

(54) NUTRIENT-ENRICHED DRESSING

(71) Applicant: SYSTAGENIX WOUND MANAGEMENT, LIMITED, West Sussex (GB)

(72) Inventors: Craig Delury, Gargrave (GB); Breda Mary Cullen, Skipton (GB); Alexander Waite, Cowling (GB); Derek Silcock, Skipton (GB)

(73) Assignee: SYSTAGENIX WOUND MANAGEMENT, LIMITED, Berkshire (GB)

( * ) Notice: Subject to any disclaimer, the term of this patent is extended or adjusted under 35 U.S.C. 154(b) by 262 days.

(21) Appl. No.: 16/760,984

(22) PCT Filed: Nov. 1, 2018

(86) PCT No.: PCT/US2018/058732
§ 371 (c)(1),
(2) Date: May 1, 2020

(87) PCT Pub. No.: WO2019/089944
PCT Pub. Date: May 9, 2019

(65) Prior Publication Data
US 2020/0306089 A1 Oct. 1, 2020

Related U.S. Application Data

(60) Provisional application No. 62/581,483, filed on Nov. 3, 2017.

(51) Int. Cl.
A61F 13/00 (2006.01)
A61L 15/28 (2006.01)
A61L 15/32 (2006.01)

(52) U.S. Cl.
CPC .. *A61F 13/00063* (2013.01); *A61F 13/00012* (2013.01); *A61F 13/00046* (2013.01);
(Continued)

(58) Field of Classification Search
None
See application file for complete search history.

(56) References Cited

U.S. PATENT DOCUMENTS 1,355,846 A 10/1920 Rannells
2,547,758 A 4/1951 Keeling
(Continued)

FOREIGN PATENT DOCUMENTS

AU 550575 B2 3/1986
AU 745271 B2 3/2002
(Continued)

OTHER PUBLICATIONS

Wong, Alvin, The Use of Specialised Amino Acid Mixture in Pressure Ulcer Wound Healing Rates—A Placebo Controlled Trial, 2013, https://clinicaltrials.gov/ct2/show/NCT01090076. (Year: 2013).*
(Continued)

*Primary Examiner* — Kim M Lewis (57) ABSTRACT

A dressing configured to be positioned adjacent to a tissue site is disclosed herein. The dressing may include oxidized regenerated cellulose (ORC), collagen, and at least one nutrient including glutamine. Methods of treating a tissue site are also disclosed herein.

23 Claims, 3 Drawing Sheets

(52) U.S. Cl.
CPC ............. *A61L 15/28* (2013.01); *A61L 15/325*
(2013.01); *A61F 2013/00255* (2013.01); *A61L 2300/104* (2013.01); *A61L 2300/404* (2013.01)

(56) References Cited

U.S. PATENT DOCUMENTS

| | | | |
|---|---|---|---|
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielsen | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carion | |
| 5,437,651 A | 8/1995 | Todd et al. | |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 6,071,267 A | 6/2000 | Zamierowski | |
| 6,135,116 A | 10/2000 | Vogel et al. | |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,814,079 B2 | 11/2004 | Heaton et al. | |
| 6,923,320 B2 * | 8/2005 | Grossman ............. A61F 15/002 206/440 |
| 11,273,077 B2 * | 3/2022 | Kubek ................... A61L 15/32 |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2015/0374878 A1 * | 12/2015 | Carter ................... A61L 27/56 156/60 |

FOREIGN PATENT DOCUMENTS

| | | | | |
|---|---|---|---|---|
| AU | 755496 B2 | 12/2002 | | |
| CA | 2005436 A1 | 6/1990 | | |
| DE | 26 40 413 A1 | 3/1978 | | |
| DE | 43 06 478 A1 | 9/1994 | | |
| DE | 29 504 378 U1 | 9/1995 | | |
| EP | 0100148 A1 | 2/1984 | | |
| EP | 0117632 A2 | 9/1984 | | |
| EP | 0161865 A2 | 11/1985 | | |
| EP | 0358302 A2 | 3/1990 | | |
| EP | 1018967 A1 | 7/2000 | | |
| EP | 1795210 A2 * | 6/2007 | ........... A61L 15/225 | |
| GB | 692578 A | 6/1953 | | |
| GB | 2 195 255 A | 4/1988 | | |
| GB | 2 197 789 A | 6/1988 | | |
| GB | 2 220 357 A | 1/1990 | | |
| GB | 2 235 877 A | 3/1991 | | |
| GB | 2 329 127 A | 3/1999 | | |
| GB | 2 333 965 A | 8/1999 | | |
| JP | 4129536 B2 | 8/2008 | | |
| SG | 71559 | 4/2002 | | |
| WO | 80/02182 A1 | 10/1980 | | |
| WO | 87/04626 A1 | 8/1987 | | |
| WO | 90/010424 A1 | 9/1990 | | |
| WO | 93/009727 A1 | 5/1993 | | |
| WO | 94/020041 A1 | 9/1994 | | |
| WO | 96/05873 A1 | 2/1996 | | |
| WO | 97/18007 A1 | 5/1997 | | |
| WO | 99/13793 A1 | 3/1999 | | |
| WO | WO-03016520 A1 * | 2/2003 | ......... C07K 14/8146 | |
| WO | WO-2004112850 A1 * | 12/2004 | ......... A61F 13/0203 | |
| WO | WO-2009/109194 A2 | 9/2009 | | |
| WO | WO-2009/128076 A2 | 10/2009 | | |
| WO | WO-2010/143646 A1 | 12/2010 | | |

OTHER PUBLICATIONS

International Search Report & Written Opinion in International Application No. PCT/US2018/058732, dated Feb. 1, 2019.

(56) References Cited

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.
Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & dated Apr. 29, 1997.
PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C. ® Therapy Clinical Guidelines: A Reference Source for Clinicians; Jul. 2007.

\* cited by examiner

NUTRIENT-ENRICHED DRESSING

CROSS-REFERENCE TO RELATED APPLICATIONS

This application is a U.S. National Phase Application under 35 U.S.C. § 371 of International Patent Application No. PCT/US2018/058732, filed on Nov. 1, 2018, which claims the benefit of priority to U.S. Provisional Patent Application No. 62/581,483, filed on Nov. 3, 2017, the contents of each of which are incorporated herein in their entirety.

TECHNICAL FIELD

The claimed subject matter relates generally to therapy of a tissue site and, more particularly, but without limitation, to compositions and devices, including dressings and dressing components, for application to a tissue site such as a wound, and to methods related to the same.

BACKGROUND

A wide variety of materials and devices, generally characterized as "dressings," are generally known in the art for use in treating a wound or other disruption of tissue. Such wounds may be the result of trauma, surgery, or disease, and may affect skin or other tissues. In general, dressings may control bleeding, absorb wound exudate, ease pain, assist in debriding the wound, protect wound tissue from infection, or otherwise promote healing and protect the wound from further damage.

Some dressings may protect tissue from, or even assist in the treatment of, infections associated with wounds. Infections can delay wound healing and, if untreated, can result in tissue loss, systemic infections, septic shock and death. While the benefits of dressings are widely accepted, improvements to dressings may benefit healthcare providers and patients.

SUMMARY

Compositions, for example, in the form of dressings, systems including such dressings, and related methods are set forth in the appended claims. Illustrative embodiments are also provided to enable a person skilled in the art to make and use the claimed subject matter.

In an aspect, a dressing is provided, which may be configured to be positioned adjacent to a tissue site, may include oxidized regenerated cellulose (ORC) and collagen. The dressing may also include at least one nutrient that includes glutamine.

In a related aspect, a method for providing therapy to a tissue site is provided where the method includes positioning a dressing adjacent to the tissue site. The dressing may include ORC, collagen, and at least one nutrient that includes glutamine.

It should be noted that the representative illustrations provided in the figures set forth herein is intended to illustrate the general features and/or characteristics of exemplary embodiments to aid in describing the present technology in full. The figures may not precisely reflect the characteristics of any given embodiment, and are not necessarily intended to define or limit the scope of the claimed subject matter. Further, the present technology may or may not include or incorporate therewith any one or more features of characteristics set provided in any one or more figures.

DETAILED DESCRIPTION

The following description provides information that enables a person skilled in the art to make and use the subject matter set forth in the appended claims, but may omit certain details already well-known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive treatment. However, as should be recognized by those skilled in the art, this frame of reference is merely a descriptive expedient rather than a strict prescription.

The present technology provides a bioresorbable, nutrient-enriched dressing and therapy systems including such dressings, as well as methods including dressings and therapy systems disclosed herein. Generally, and as will be disclosed herein, the dressings of the present technology may be configured to provide therapy to a tissue site.

The following terms are used throughout as defined below.

As used herein and in the appended claims, singular articles such as "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 atoms refers to groups having 1, 2, or 3 atoms. Similarly, a group having 1-5 atoms refers to groups having 1, 2, 3, 4, or 5 atoms, and so forth.

As understood by one of ordinary skill in the art, "molecular weight" (also known as "relative molar mass") is a dimensionless quantity but is converted to molar mass by multiplying by 1 gram/mole—for example, collagen with a weight-average molecular weight of 5,000 has a weight-average molar mass of 5,000 g/mol.

As used herein, "tissue site" is intended to broadly refer to a wound, defect, or other treatment target located on or within tissue, including but not limited to, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds, partial-thickness burns, ulcers (such as diabetic, pressure, or venous insufficiency ulcers), flaps, and grafts, for example. The term "tissue site" may also refer to areas of any tissue that are not necessarily wounded or defective, but are instead areas in which it may be desirable to add or promote the growth of additional tissue.

As used herein, the term "effective amount" refers to a quantity sufficient to achieve a desired therapeutic effect, e.g., an amount which results in the decrease in a wound described herein or one or more signs or symptoms associated with a wound described herein. In the context of therapeutic applications, the amount of a composition administered to the subject will vary depending on the composition, the degree, type, and severity of the wound and on the characteristics of the individual. The compositions can also be administered in combination with one or more additional therapeutic compounds. In the methods described herein, the therapeutic compositions may be administered to a subject having one or more wounds.

As used herein, the terms "individual", "patient", or "subject" can be an individual organism, vertebrate, a mammal, or a human. In some embodiments, the individual, patient, or subject is a human.

"Treating" or "treatment" as used herein includes: (i) inhibiting a wound of a subject, i.e., arresting its development; (ii) relieving a wound of a subject, i.e., causing regression of the wound; (iii) slowing progression of a wound of a subject; and/or (iv) inhibiting, relieving, and/or slowing progression of one or more symptoms of a wound of a subject. Such treatment means that the symptoms associated with the wound are, e.g., alleviated, reduced, cured, or placed in a state of remission.

It is also to be appreciated that the various modes of treatment of wounds as described herein are intended to mean "substantial," which includes total but also less than total treatment, and wherein some biologically or medically relevant result is achieved. The treatment may be a continuous prolonged treatment for a chronic wound or a single, or few time administrations for the treatment of an acute wound.

Dressings of the Present Technology

Figure 1:
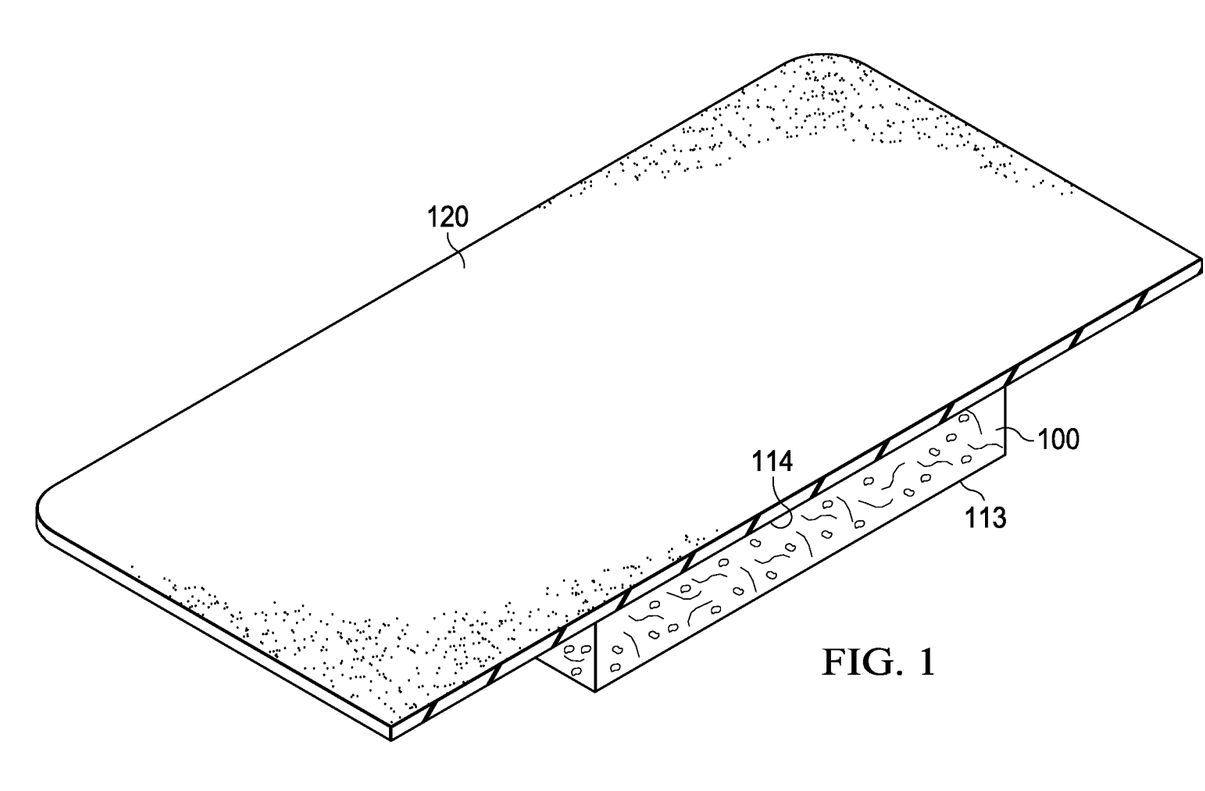
FIG. 1 is a cross-sectional, perspective view of an example embodiment a dressing in accordance with this specification.

In an aspect, the present technology provides a dressing that may be configured or may include one or more layers configured to interface with a tissue site, where the dressing includes oxidized regenerated cellulose (ORC), collagen, and at least one nutrient that includes glutamine. FIG. 1 provides an illustrative illustration of a dressing 100, that may generally be configured to be positioned adjacent to a tissue site, for example, to be in contact with a tissue site. In any embodiment herein, the dressing may be configured so as to be in contact with a portion of a tissue site, substantially all of a tissue site, or a tissue site in its entirety. For example, in any embodiment herein, if the tissue site is a wound, the dressing may partially or completely fill the wound, or may be placed over the wound. In any embodiment herein, the dressing may take many forms, and may have many sizes, shapes, or thicknesses depending on a variety of factors, such as the type of treatment being implemented or the nature and size of a tissue site. For example, in any embodiment herein, the size and shape of the dressing may be adapted to the contours of deep and irregular shaped tissue sites, may be configured so as to be adaptable to a given shape or contour, or combinations thereof. In any embodiment herein, any or all of the surfaces of the dressing may include projections or an uneven, course, or jagged profile that may induce strains and stresses on a tissue site, for example, which may be effective to promote granulation at the tissue site.

In any embodiment, the dressing may be in a substantially sheet form. For example, in any embodiment herein, the dressing may include a generally planar structure having two opposite-facing planar surfaces and a thickness orthogonal to the planar surfaces. As used herein, "planar surface" refers to surfaces that are generally recognized as flat or capable of being laid flat. In any embodiment herein, the dressing may include a first surface and a second surface, where the first surface, second surface, or both may be substantially planar. FIG. 1, for example, illustrates a dressing 100 including a first surface 113 and a second surface 114, where the first surface 113, the second surface 114, or both may be substantially planer. In any embodiment herein, the first surface, the second surface, or both may be configured to face a tissue site. In any embodiment herein, the first surface, the second surface, or both may have a surface area from about 1 $cm^2$ to about 400 $cm^2$, such as from about 2 $cm^2$ to about 200 $cm^2$ or from about 4 $cm^2$ to about 100 $cm^2$; thus, the surface area of the first surface, the second surface, or both included in any embodiment herein may have a surface area of about 1 $cm^2$, about 2 $cm^2$, about 3 $cm^2$, about 4 $cm^2$, about 5 $cm^2$, about 6 $cm^2$, about 7 $cm^2$, about 8 $cm^2$ about 9 $cm^2$, about 10 $cm^2$, about 11 $cm^2$, about 12 $cm^2$, about 13 $cm^2$, about 14 $cm^2$, about 15 $cm^2$, about 16 $cm^2$, about 17 $cm^2$, about 18 $cm^2$, about 19 $cm^2$, about 20 $cm^2$, about 25 $cm^2$ about 30 $cm^2$, about 40 $cm^2$, about 50 $cm^2$, about 55 $cm^2$, about 60 $cm^2$, about 65 $cm^2$, 70 $cm^2$, about 75 $cm^2$, about 80 $cm^2$, about 85 $cm^2$, about 90 $cm^2$, about 95 $cm^2$, about 100 $cm^2$, about 150 $cm^2$, about 200 $cm^2$, about 250 $cm^2$, about 300 $cm^2$, about 350 $cm^2$, about 400 $cm^2$, or any range including and/or in between any two of the preceding values. In any embodiment herein, the first surface and the second surface may have any suitable shape, including but not limited to, triangles, squares, rectangles, ellipses, circles, ovals, or various polygons having four, five, six, seven, eight, or more sides. In any embodiment herein, the shape and area of the first surface and the second surface may be customized to the location and type of tissue site onto which the dressing is to be applied.

In any embodiment herein, the dressing may be in the form of a film or a sponge, or combinations thereof. For example, in any embodiment herein, the dressing may include a sponge that includes pores having an average pore size according to the needs of a prescribed therapy. For example, in any embodiment herein, the average pore size may be in a range from about 200 µm to about 3000 µm; thus, the average pore size in any embodiment herein may be about 200 µm, about 300 µm, about 400 µm, about 500 µm, about 600 µm, about 700 µm, about 800 µm, about 900 µm, about 1000 µm, about 1200 µm, about 1400 µm, about 1600 µm, about 1800 µm, about 2000 µm, about 2200 µm, about 2400 µm, about 2600 µm, about 2800 µm, about 3000 µm, or any range including and/or in between any two of the preceding values. Additionally or alternatively, in some embodiments, the dressing may have various physical properties, such as tensile strength, as will be suitable according to needs of a prescribed therapy.

Composition

In any embodiment herein, the dressing may be characterized as being biodegradable and/or as exhibiting biodegradability. As used herein, "biodegradable" and "biodegradability" may refer to a characteristic of a material to at least partially break down upon exposure to physiological fluids or processes. For example, in any embodiment herein, the dressing may disintegrate, degrade, or dissolve when contacted with an aqueous medium, such as water, blood, or wound exudate from a tissue site. Biodegradability may be a result of a chemical process or condition, a physical process or condition, or combinations thereof.

Additionally or alternatively, in any embodiment herein, the dressing may be characterized as being bioresorbable and/or as exhibiting bioresorbability. As used herein, "bioresorbable" and "bioresorbability" may refer to a characteristic of a material to be broken down into degradation products that may be absorbed at a tissue site so as to be eliminated by the body, for example via metabolism or excretion. In any embodiment herein, the bioresorbable characteristics of the dressing may be such that at least a portion of the dressing or the material from which the dressing is formed may be eliminated from the tissue site to which it is applied by bioresorption.

In any embodiment, a portion or all of the dressing may be configured to exhibit a particular proportion of disintegration, degradation, and/or dissolution (hereinafter referred to as "broken down") within a particular time period. In any embodiment herein, the dressing may be configured such that about 90% by weight, more particularly, about 95% by weight, more particularly, about 99% by weight, more particularly, about 100% by weight of the dressing may be broken down within a time period from about 24 hours to about 7 days, from introduction into a physiological environment or when incubated with simulated physiological fluid at a temperature of about 37° C. For example, in any embodiment herein, the dressing may be configured such that about 90% by weight, about 91% by weight, about 92% by weight, about 93% by weight, about 94% by weight, about 95% by weight, about 96% by weight, about 97% by weight, about 98% by weight, about 99% by weight, or about 100% by weight of the dressing (or any range including and/or in between any two of the preceding values) may be broken down within a time period of about 24 hours, about 26 hours, about 28 hours, about 30 hours, about 32 hours, about 34 hours, about 36 hours, about 38 hours, about 40 hours, about 42 hours, about 44 hours, about 46 hours, about 2 days, about 3 days, about 4 days, about 5 days, about 6 days, or about 7 days (or any range including and/or in between any two of the preceding values) from introduction into a physiological environment or when incubated with simulated physiological fluid at a temperature of about 37° C. Additionally or alternatively, in some embodiments, a portion or all of the dressing may be non-bioresorbable.

In any embodiment herein, when the dressing is used in a therapy, the dressing may be configured to modulate protease activity. For example, in any embodiment herein, contacting the dressing with wound fluid, such as wound exudate, may cause the dressing to break down into products that may have the effect of modulating protease activity. In any embodiment herein, modulating protease activity may include inhibiting protease activity. For example, in any embodiment herein, the disintegration, degradation, and/or dissolution products of collagen and/or ORC may be effective to inhibit the activity of destructive enzymes, including but not limited to, destructive enzymes such as neutrophil elastase and matrix metalloproteinase (MMP). In any embodiment herein, the dressing may be effective to inhibit protease activity such that protease activity is decreased to less than about 75% of the protease activity that would be present if uninhibited. For example, in any embodiment herein, the protease activity may be decreased to less than about 75%, less than about 70%, less than about 65%, less than about 60%, less than about 55%, less than about 50%, less than about 45% less than about 40%, less than about 35%, less than about 30%, less than about 25%, less than about 20%, less than about 15%, less than about 10%, less than about 9%, less than about 8%, less than about 7%, less than about 6%, less than about 5%, less than about 4%, less than about 3%, less than about 2%, less than about 1% or any range including and/or in between any two of the preceding values) of the protease activity than would be present if uninhibited.

In any embodiment herein, the dressing may include or be formed at least partially from a suitable composition, which may be referred to herein as the dressing composition. For example, in any embodiment herein, the dressing composition may make up the sponge, film, or other structure of the dressing.

In any embodiment herein, the dressing composition may include oxidized cellulose, such as ORC. Oxidized cellulose may be produced by the oxidation of cellulose, for example with dinitrogen tetroxide. Not intending to be bound by theory, this process may convert primary alcohol groups on the saccharide residues to carboxylic acid groups, forming uronic acid residues within the cellulose chain. The oxidation may not proceed with complete selectivity, and as a result hydroxyl groups on carbons 2 and 3 may be converted to the keto form. These ketone units yield an alkali labile link, which at pH 7 or higher initiates the decomposition of the polymer via formation of a lactone and sugar ring cleavage. As a result, oxidized cellulose may be biodegradable and bioabsorbable under physiological conditions.

In any embodiment herein, the oxidized cellulose may be ORC prepared by oxidation of a regenerated cellulose, such as rayon. Suitable ORC and processes of manufacturing the same are disclosed in U.S. Pat. No. 3,122,479, incorporated herein by reference in its entirety. ORC is available with varying degrees of oxidation and hence rates of degradation.

In any embodiment herein, the ORC may be in the form of water-soluble low molecular weight fragments obtained by alkali hydrolysis of ORC.

In any embodiment herein, the ORC may be used in a variety of physical forms, including but not limited to, particles, fibers, sheets, sponges, fabrics, or combinations of two or more thereof. In any embodiment herein, the ORC may be in the form of particles, such as fiber particles or powder particles, for example, dispersed in a suitable solid or semisolid topical medicament vehicle. In any embodiment herein, the dressing compositions may include ORC fibers, wherein a volume fraction of at least 80% of the fibers have lengths in the range from about 5 µm to about 50 mm. For example, in any embodiment herein, the ORC fibers may have a volume fraction of at least 80% of the fibers having lengths in the range from about 5 µm to about 50 mm, about 20 µm to about 50 mm, about 25 mm to about 50 mm, about 5 µm to about 1000 µm, about 250 µm to about 450 µm, or any range including and/or in between any two of the preceding values. In any embodiment herein, a volume fraction of at least 80% of the fibers have lengths in the range from about 5 µm, about 10 µm, about 15 µm, about 20 µm, about 25 µm, about 30 µm, about 35 µm, about 40 µm, about 45 µm, about 50 µm, about 55 µm, about 60 µm, about 65 µm, about 70 µm, about 75 µm, about 80 µm, about 85 µm, about 90 µm, about 95 µm, about 100 µm, about 150 µm, about 200 µm, about 250 µm, about 300 µm, about 350 µm, about 400 µm, about 450 µm, about 500 µm, about 550 µm, about 600 µm, about 650 µm, about 700 µm, about 750 µm, about 800 µm, about 850 µm, about 900 µm, about 950 µm, about 1000 µm, about 5 mm, about 10 mm, about 15 mm, about 20 mm, about 25 mm, about 30 mm, about 35 mm, about 40 mm, about 45 mm, about 50 mm, or any range including and/or in between any two of the preceding values. In any embodiment herein, desired size distributions may be achieved, for example, by milling an ORC cloth, followed by sieving the milled powder to remove fibers outside the range. In any embodiment herein, fabrics may include woven, non-woven, or knitted fabrics.

In any embodiment herein, the ORC may be present in the dressing composition at any level appropriate to result in the desired absorbency and rheological characteristics of the dressing composition or the dressing. For example, in any embodiment herein, the ORC may be present in the dressing at a level from about 10% to about 80% by weight of the dressing, such as from about 30% to about 60% by weight or from about 40% to about 50% by weight of the dressing; thus, the ORC may be present in the dressing at a level included in any embodiment herein from about 10% by weight, about 15% by weight, about 20% by weight, about 25% by weight, about 30% by weight, about 35% by weight, about 40% by weight, about 45% by weight, about 50% by weight, about 55% by weight, about 60% by weight, about 65% by weight, about 70% by weight, about 75% by weight, about 80% by weight (or any range including and/or in between any two of the preceding values) of the dressing.

In any embodiment herein, the dressing composition may include a structural protein. For example, in any embodiment herein, suitable structural proteins may include, but are not limited to, fibronectin, fibrin, laminin, elastin, collagen, gelatins, or mixtures of two or more thereof. In any embodiment herein, the structural protein may include collagen. The collagen may be obtained from any natural source. In any embodiment herein, the collagen may be Type I, II or III collagen, or may also be chemically modified collagen; for example, in any embodiment herein, the chemically modified collagen may include an atelocollagen obtained by removing the immunogenic telopeptides from natural collagen. In any embodiment, the collagen may further include solubilized collagen or soluble collagen fragments having molecular weights in the range from about 5,000 to about 100,000, such as from about 10,000 to about 50,000, where the solubilized collagen or soluble collagen fragments may be obtained, for example, by pepsin treatment of natural collagen. The collagen in the dressing composition may have, in any embodiment herein, a weight-average molecular weight of about 5,000, about 6,000, about 7,000, about 8,000, about 9,000, about 10,000, about 12,000, about 14,000, about 16,000, about 18,000, about 20,000, about 22,000, about 24,000, about 26,000, about 28,000, about 30,000, about 32,000, about 34,000, about 36,000, about 38,000, about 40,000, about 45,000, about 50,000, about 55,000, about 60,000, about 65,000, about 70,000, about 75,000, about 80,000, about 85,000, about 90,000, about 95,000, about 100,000, or any range including and/or in between any two of these values. In any embodiment herein, the collagen is obtained from bovine corium that has been rendered largely free of non-collagenous components. Such non-collagenous components may include fat, non-collagenous proteins, polysaccharides and other carbohydrates, as described in U.S. Pat. Nos. 4,614,794 and 4,320,201, incorporated by reference herein.

In any embodiment herein, the collagen or other structural protein may be present in the dressing at any level appropriate. For example, in any embodiment herein, the collagen or other structural protein may be present in the dressing at a level from about 20% to about 90% by weight, such as from about 40% to about 70% by weight, from about 50% to about 60% by weight, or about 55% collagen by weight of the dressing; thus, in any embodiment herein, the collagen or structural protein may be present in the dressing at a level from about 20% by weight, about 25% by weight, about 30% by weight, about 35% by weight, about 40% by weight, about 45% by weight, about 50% by weight, about 55% by weight, about 60% by weight, about 65% by weight, about 70% by weight, about 75% by weight, about 80% by weight, about 85% by weight, about 90% by weight, or any range including and/or in between any two of the preceding values.

In any embodiment herein, the dressing composition may include both ORC and collagen. For example, in any embodiment, the dressing may include ORC at a level from about 40% to about 50%, such as about 45% by weight, and collagen at a level from about 50% to about 60% by weight, such as about 55% by weight, of the dressing. Thus, in any embodiment herein, the dressing may include ORC at a level from about 40% by weight, about 41% by weight, about 42% by weight, about 43% by weight, about 44% by weight, about 45% by weight, about 46% by weight, about 47% by weight, about 48% by weight, about 49% by weight, about 50% by weight (or any ranges including and/or in between any two of the preceding values) of the dressing, and collagen at a level from about 50% by weight, about 51% by weight, about 52% by weight, about 53% by weight, about 54% by weight, about 55% by weight, about 56% by weight, about 57% by weight, about 58% by weight, about 59% by weight, about 60% by weight (or any ranges including and/or in between any two of the preceding values) of the dressing.

Additionally or alternatively, in any embodiment herein, the dressing composition may include a bioresorbable polysaccharide. For example, in any embodiment herein, bioresorbable polysaccharides include, but are not limited to, alginates, chitosan, chitin, guar gums, starch, starch derivatives, ß-Glucans, cellulose derivatives, glycosaminoglycans, chondroitin sulfate, heparin sulfate, pectins, or combinations of two or more thereof.

In any embodiment herein, the bioresorbable polysaccharide may include chitosan. Chitosan is derived from the natural biopolymer, chitin, which may be described as being composed of N-acetyl-D-glucosamine units. Chitin may be extracted from the outer shell of shrimp or crab in a known fashion. The chitin may then be partially deacetylated, for example by treatment with sodium hydroxide, to produce chitosan. Complete deacetylation of the chitin is not a practical possibility, but the chitosan may be at least 50% deacetylated, or at least 75% deacetylated. Chitosan in the free base form may be swellable but not substantially soluble in water at near-neutral pH, but soluble in acids due to the presence of ammonium groups on the chitosan chain. The solubility of the chitosan may be reduced by cross-linking, for example with epichlorohydrin. Typically, the average molecular weight of the chitosan as determined by gel permeation chromatography may be from about $10^5$ to about $10^6$.

In any embodiment herein, the dressing composition may further include chitosan present at any level appropriate to result in the desired absorbency and rheological characteristics of the dressing composition or the dressing. For example, in any embodiment herein, the chitosan may be present in the dressing at a level from about 10% to about 100% by weight, such as from about 30% to about 90% by weight or from about 40% to about 85% by weight of the dressing; thus, in any embodiment herein, the chitosan may be present in the dressing at a level, including but not limited to, from about 10% by weight, about 15% by weight, about 20% by weight, about 25% by weight, about 30% by weight, about 35% by weight, about 40% by weight, about 45% by weight, about 50% by weight, about 55% by weight, about 60% by weight, about 65% by weight, about 70% by weight, about 75% by weight, about 80% by weight, about 85% by weight, about 90% by weight, about 95% by weight, about 100% by weight (or any ranges including and/or in between any two of the preceding values) of the dressing.

Additionally, in any embodiment herein, the dressing composition may further include one or more additional, optional materials. For example, in any embodiment herein, such optional components may include, but are not limited to, preservatives, stabilizing agents, hydrogels, other gelling agents, plasticizers, matrix strengthening materials, dyestuffs, various active ingredients, or mixtures of two or more thereof. In any embodiment herein, the additional, optional materials may each, when present, be present in a safe and effective amount. As referred to herein, a "safe and effective" amount of a material refers to an amount that is sufficient to impart a desired effect without undue adverse side effects (such as toxicity, irritation, or allergic response), commensurate with a reasonable benefit/risk ratio when used in the manner of this technology. The specific safe and effective amount of a particular material may vary with such factors as the type and quantity of other materials in the dressing composition, the intended use, and the physical condition of the subject to whom the dressing compositions are given, and the form in which the dressing compositions are employed.

For example, in any embodiment herein, the dressing composition may include an optional gelling agent. Suitable gelling agents include, but are not limited to, hydrophilic polysaccharides. For example, in any embodiment herein, the hydrophilic polysaccharides may include, but are not limited to, alginates, chitosan, chitin, guar gums, pectin, starch derivatives, cellulose derivatives (such as hydroxyethyl cellulose, hydroxylpropyl cellulose, and hydroxypropylmethyl cellulose), glycosaminoglycans, galactomannans, chondroitin salts (such as chondroitin sulfate), heparin salts (such as heparin sulfate), hyaluronic acid or salts thereof, hyaluronates, or mixtures of two or more thereof.

In any embodiment herein, the dressing composition may include carboxymethyl cellulose ("CMC"), which may be included to modify the rheological, absorbency, or other characteristics of the dressing composition or the dressing. The CMC may be derived from cellulose and modified such that carboxymethyl groups are bonded to hydroxyl groups in the glucopyranose monomers that make up the cellulose. In any embodiment herein, the CMC may be in salt form; for example, in any embodiment herein, the CMC may include a physiologically acceptable cation, such as sodium (i.e., sodium carboxymethyl cellulose). CMC is commercially available as Walocel™ (sold by The Dow Chemical Company) and Cekol® (sold by CP Kelco). In any embodiment herein, the CMC may be present in the dressing composition at any level appropriate to result in the desired characteristics.

In any embodiment herein, the dressing composition may include a strengthening material, where the strengthen material may be included to improve the handling characteristics of the substrate by decreasing the susceptibility of the dressing to tearing. For example, in any embodiment herein, a suitable strengthening material may include, but is not limited to, non-gelling cellulose fibers. Such "non-gelling" cellulose fibers may be substantially water-insoluble, and may be produced from cellulose that has not been chemically modified to increase water solubility (as contrasted from carboxymethyl cellulose or other cellulose ethers). Non-gelling cellulose fibers are commercially available as Tencel® fibers (sold by Lenzing AG). In any embodiment herein, the non-gelling cellulose fibers may be processed from a commercially-available continuous length by cutting into lengths that are from about 0.5 to about 5 cm, such as from about 2 to about 3 cm in length. For example, in any embodiment herein, the non-gelling cellulose fibers may have a length from about 0.5 cm, about 1 cm, about 1.5 cm, about 2 cm, about 2.5 cm, about 3 cm, about 3.5 cm, about 4 cm, about 4.5 cm, about 5 cm, or any range including and/or in between any two of the preceding values. In any embodiment herein, the non-gelling cellulose fibers may be present in the dressing composition at any level appropriate to result in the desired physical characteristics of the dressing.

In any embodiment herein, the dressing composition may also include one or more active ingredients which aid in wound healing. For example, in any embodiment herein, the active ingredients may include, but are not limited to, non-steroidal anti-inflammatory drugs, acetaminophen, steroids, optional antibiotics and antiseptics (e.g., silver and chlorhexidine), or growth factors (e.g., fibroblast growth factor or platelet derived growth factor). In general, such active ingredients, when present in any embodiment herein, may be present at a level from about 0.1% to about 10% by weight of the dressing. For example, in any embodiment herein, the active ingredients may present at a level from about 0.1%, about 0.2%, about 0.3%, about 0.4%, about 0.5%, about 06%, about 0.7%, about 0.8%, about 0.9%, about 1%, about 1.5%, about 2%, about 2.5%, about 3%, about 3.5%, about 4%, about 4.5%, about 5%, or any range including and/or in between any two of the preceding values. In any embodiment herein, the dressing composition may include a growth factor. Suitable growth factors may include, but are not limited to, platelet derived growth factor (PDGF), fibroblast growth factor (FGF), epidermal growth factor (EGF), or mixtures of two or more thereof.

In any embodiment herein, the dressing composition may include an antimicrobial agent, an antiseptic, or a combination thereof. Suitable antimicrobial agents may include, but are not limited to, tetracycline, penicillin, terramycins, erythromycin, bacitracin, neomycin, polymycin B, mupirocin, clindamycin, or combinations of two or more thereof. Suitable antiseptics may include, but are not limited to, silver, chlorhexidine, povidone iodine, triclosan, sucralfate, quaternary ammonium salts, or combinations of two or more thereof. For example, in any embodiment herein, the dressing composition may include silver. In any embodiment herein, the silver may be in metallic form, in ionic form (e.g., a silver salt), or both. For example, in any embodiment herein, the silver may be present in ionic form. In any embodiment herein, the dressing composition may include a complex of silver and ORC (a "Silver/ORC complex"). As referred to herein, such a complex is an intimate mixture at the molecular level, for example, with ionic or covalent bonding between the silver and the ORC. For example, in any embodiment herein, the Silver/ORC complex may include a salt formed between the ORC and $Ag^+$. Additionally or alternatively, in any embodiment herein, the Silver/ORC may further include silver clusters or colloidal silver metal, for example produced by exposure of the complex to light. The complex of an anionic polysaccharide and silver can be made by treating the ORC with a solution of a silver salt. In any embodiment herein, the silver salt may be the salt of silver with a weak acid. Silver/ORC complexes useful herein, and methods of producing such complexes, are described in U.S. Pat. No. 8,461,410, incorporated by reference herein. Similar processes are described in U.S. Pat. No. 5,134,229, incorporated by reference herein. In any embodiment herein, the Silver/ORC Complex may be present in the dressing at a level from about 1% to about 2% by weight of the dressing. For example, in any embodiment herein, the Silver/ORC Complex may be present in the dressing at a level from about 1% by weight, about 1.1% by weight, about 1.2% by weight, about 1.3% by weight, about 1.4% by weight, about 1.5% by weight, about 1.6% by weight, about 1.7% by weight, about 1.8% by weight, about 1.9% by weight, about 2% by weight (or any range including and/or in between any two of the preceding values) of the dressing. Alternatively, in any embodiment herein, the dressing composition may not contain an antimicrobial agent or an antiseptic.

In any embodiment herein, the dressing composition may include a dyestuff. For example, in any embodiment herein, the dyestuff may be light-absorbing in the visible region 400-700 nm. Such dyestuffs may be operable to photochemically trap generated free radicals that could otherwise react with the silver in the present compositions, acting as photochemical desensitisers. In any embodiment herein, the antioxidant dyestuff may include, but is not limited to, aniline dyes, acridine dyes, thionine dyes, bis-naphthalene dyes, thiazine dyes, azo dyes, anthraquinone dyes, or mixtures of two or more thereof. For example, in any embodiment herein, the antioxidant dyestuff may include gentian violet, aniline blue, methylene blue, crystal-violet, acriflavine, 9-aminoacridine, acridine yellow, acridine orange, proflavin, quinacrine, brilliant green, trypan blue, trypan red, malachite green, azacrine, methyl violet, methyl orange, methyl yellow, ethyl violet, acid orange, acid yellow, acid blue, acid red, thioflavin, alphazurine, indigo blue, methylene green, and mixtures thereof. In any embodiment herein, the dyestuff may be present in the dressing at a level of about 0.05% to about 5%, such as about 0.2% to about 2% by weight of the dressing. For example, in any embodiment herein, the dyestuff may be present in the dressing at a level of about 0.05% by weight, about 0.1% by weight, about 0.2% by weight, about 0.3% by weight, about 0.4% by weight, about 0.5% by weight, about 0.6% by weight, about 0.7% by weight, about 0.8% by weight, about 0.9% by weight, about 1% by weight, about 1.5% by weight, about 2% by weight, about 2.5% by weight, about 3% by weight, about 3.5% by weight, about 4% by weight, about 4.5% by weight, about 5% by weight (or any ranges including and/or in between any two of the preceding values) of the dressing.

In any embodiment herein, the dressing may be essentially free of water. Alternatively, in any embodiment herein, a composition from which the dressing is formed may include up to about 20% water. For example, in any embodiment herein, the composition from which the dressing is formed may include about 20% or less, about 19% or less, about 18% or less, about 17% or less, about 16% or less, about 15% or less, about 14% or less, about 13% or less, about 12% or less, about 11% or less, about 10% or less, 9% or less, about 8% or less, about 7% or less, about 6% or less, about 5% or less, about 4% or less, about 3% or less, about 2% or less, about 1% or less, about 0.5% or less, about 0.01% or less (or any range including and/or in between any two of the preceding values) of water. In any embodiment herein, the dressing may be freeze-dried. For example, in any embodiment, the dressing may be freeze-dried through lyophilization, for example.

Nutrient

In any embodiment herein, the dressing may further include a nutrient. As used herein, "nutrient" refers broadly to any substance that may be utilized by a population of cells during cell growth and proliferation, for example, during healing a tissue at the tissue site (e.g., a wound site). Suitable nutrients may, but are not limited to, include amino acids, vitamins, minerals, fatty acids, or mixtures of two or more thereof.

In any embodiment herein, the nutrient may be applied to the dressing as a constituent that may be separate from the dressing composition. For example, in any embodiment herein, the nutrient may be applied to one or more surfaces of the dressing. In any embodiment herein, the nutrient may be formulated in a suitable physical form; for example, the nutrient may be formulated as a particulate such as a powder, a granule, or a fiber, or as a liquid which may be dissolved or suspended in a solution. In any embodiment herein, the nutrient may, when formulated, be applied to at least some of the surfaces of the dressing. In any embodiment herein, the nutrient may be applied to all or substantially all of the surfaces of the dressing. Alternatively, in any embodiment, the nutrient may be applied to only a portion of the surfaces of the dressing. For example, in any embodiment herein, the nutrient may be applied to localized, particular portions of a bioresorbable structure. For example, as illustrated in FIG. 1, the nutrient may be applied to localized, particular portions of the first surface 113, or to a proportion of the dressing 100 nearest the first surface 113. In any embodiment herein, the nutrient may be applied to about 50% by volume of the dressing nearest a first surface, such as about 25% by volume of the dressing nearest a first surface. For example, in any embodiment herein, the nutrient may be applied to about 50%, about 45%, about 40%, about 35%, about 30%, about 25%, about 20%, about 15%, about 10%, about 5%, about 1% (or any range including and/or in between any two of the preceding values) by volume of the dressing nearest a first surface.

Additionally or alternatively, in any embodiment herein, the nutrient may be included within a film applied to one or more surfaces of the dressing. For example, in any embodiment herein, the film may be applied to a first surface of the dressing. In any embodiment herein, the film may have a suitable thickness, including but not limited to, from about 100 μm to about 3000 μm; thus, in any embodiment herein, the film may have a thickness of about 100 μm, about 200 μm, about 300 μm, about 400 μm, about 500 μm, about 600 μm, about 700 μm, about 800 μm, about 900 μm, about 1000 μm, about 1100 μm, about 1200 μm, about 1300 μm, about 1400 μm, about 1500 μm, about 1600 μm, about 1700 μm, about 1800 μm, about 1900 μm, about 2000 μm, about 2100 μm, about 2200 μm, about 2300 μm, about 2400 μm, about 2500 μm, about 2600 μm, about 2700 μm, about 2800 μm, about 2900 μm, about 3000 μm, or any range including and/or in between any two of the preceding values. In any embodiment herein, the film may be characterized as impermeable to fluids or substantially impermeable to fluids (e.g., a non-porous film). In any embodiment herein, the film may be configured to allow the passage of a fluid. For example, the film may include a plurality of pores extending therethrough so as to allow communication through the film. The plurality of pores may have an average pore size in the range from about 200 μm to about 3000 μm; thus, the average pore size in any embodiment herein may be about 200 μm, about 300 μm, about 400 μm, about 500 μm, about 600 μm, about 700 μm, about 800 μm, about 900 μm, about 1000 μm, about 1200 μm, about 1400 μm, about 1600 μm, about 1800 μm, about 2000 μm, about 2200 μm, about 2400 μm, about 2600 μm, about 2800 μm, about 3000 μm, or any range including and/or in between any two of the preceding values. The film may include a plurality of pores at a pore density in the range from about 2 pores/cm$^2$ to about 10 pores/cm$^2$; thus, the film of any embodiment herein may have a pore density of about 2 pores/cm$^2$, about 4 pores/cm$^2$, about 6 pores/cm$^2$, about 8 pores/cm$^2$, about 10 pores/cm$^2$, or any range including and/or in between any two of the preceding values.

Additionally or alternatively, in any embodiment herein, the nutrient may be included within the dressing composition, such that the nutrient is a component of the bioresorbable structure itself or a portion of the bioresorbable structure.

The nutrient may be generally present in a safe and effective amount. The particular amount of the nutrient may depend upon the particular nutrient or combination of nutrients present. For example, in any embodiment herein, the nutrient may be present in an amount from about 0.1 grams per gram of the bioresorbable components to about 1 gram per gram of bioresorbable components. For example, in any embodiment herein, the nutrient may be present in an amount from about 0.1 grams per gram of the combined collagen and ORC to about 1 gram per gram of the combined collagen and ORC; thus, the nutrient may be present in an amount in any embodiment herein from about 0.1 grams, about 0.2 grams, about 0.3 grams, about 0.4 grams, about 0.5 grams, about 0.6 grams, about 0.7 grams, about 0.8 grams, about 0.9 grams, about 1 gram (or any range including and/or in between any two of the preceding values) per gram of the combined collagen and ORC.

In any embodiment herein, the nutrient may include an amino acid. Suitable amino acids may include, but are not limited to, alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, valine, or combinations of two or more thereof. In any embodiment herein, the nutrient may include glutamine and/or at least one other amino acid. For example, in any embodiment herein, the nutrient may include glutamine and one or more of alanine, arginine, asparagine, aspartic acid, cysteine, glutamic acid, glycine, histidine, isoleucine, leucine, lysine, methionine, phenylalanine, proline, serine, threonine, tryptophan, tyrosine, or valine. For example, in any embodiment herein, the nutrient may include glutamine and arginine.

In any embodiment herein, the nutrient may include a mineral; for example, in any embodiment herein, the mineral may include, but is not limited to, calcium, phosphorus, potassium, sodium, chlorine, magnesium, iron, cobalt, copper, zinc, manganese, molybdenum, iodine, selenium, or combinations of two or more thereof. In any embodiment herein, the nutrient includes glutamine and at least one mineral. For example, in any embodiment herein, the nutrient may include glutamine and one or more of calcium, phosphorus, potassium, sodium, chlorine, magnesium, iron, cobalt, copper, zinc, manganese, molybdenum, iodine, or selenium.

In any embodiment herein, the nutrient may include a vitamin. Suitable vitamins include, but are not limited to, vitamin A, vitamin $B_1$, vitamin $B_2$, vitamin $B_3$, vitamin $B_5$, vitamin $B_6$, vitamin $B_7$, vitamin $B_9$, vitamin $B_{12}$, vitamin $B_1$, vitamin C, vitamin D, vitamin E, vitamin K, or combinations thereof. In some, more particular embodiments, the nutrient comprises glutamine and at least one vitamin. For example, in some embodiments, the nutrient comprises glutamine and one or more of vitamin A, vitamin $B_1$, vitamin $B_2$, vitamin $B_3$, vitamin $B_5$, vitamin $B_6$, vitamin $B_7$, vitamin $B_9$, vitamin $B_{12}$, vitamin $B_1$, vitamin C, vitamin D, vitamin E, or vitamin K.

In any embodiment herein, the nutrient may include a fatty acid. For example, in any embodiment herein, the fatty acid may include a short-chain polyunsaturated fatty acid, including but not limited to, alpha-linolenic acid (e.g., an omega-3 fatty acid), linoleic acid (e.g., an omega-6 fatty acid), a long-chain polyunsaturated fatty acid such as eicosapentaenoic acid (e.g., an omega-3 fatty acid), docosahexaenoic acid (e.g., an omega-3 fatty acid), gamma-linolenic acid (e.g., an omega-6 fatty acid), dihomo-gamma-linolenic acid (e.g., an omega-6 fatty acid), arachidonic acid (e.g., an omega-6 fatty acid), or combinations of two or more thereof. In any embodiment herein, the nutrient may include glutamine and at least one fatty acid. For example, in any embodiment herein, the nutrient may include glutamine and one or more of alpha-linolenic acid or linoleic acid.

In any embodiment herein, the dressing may include collagen and ORC and a nutrient applied thereto, so as to coat at least a portion of the exposed surfaces of the dressing. For example, in any embodiment herein, the dressing may be in the form of a sponge. In any embodiment herein, the dressing may include collagen in an amount from about 50% to about 60% by weight, ORC in an amount from about 40% to about 50% by weight and, optionally, silver in an amount from about 0.25% to about 2% by weight of the dressing. Thus, in any embodiment herein, the dressing may include ORC at a level from about 40% by weight, about 41%, about 42%, about 43%, about 44%, about 45%, about 46%, about 47%, about 48%, about 49%, about 50% (or any ranges including and/or in between any two of the preceding values) by weight of the dressing, collagen at a level from about 50%, about 51%, about 52%, about 53%, about 54%, about 55%, about 56%, about 57% about 58%, about 59%, about 60% (or any ranges including and/or in between any two of the preceding values) by weight of the dressing, and, optionally, silver in an amount from about 0.25%, about 0.3%, about 0.4%, about 0.5%, about 0.6%, about 0.7%, about 0.8%, about 0.9%, about 1%, about 1.1%, about 1.2%, about 1.3%, about 1.4%, about 1.5%, about 1.6%, about 1.7%, about 1.8%, about 1.9%, about 2% (or any range including and/or in between any two of the preceding values) by weight of the dressing. In any embodiment herein, suitable dressings that include collagen and ORC include, but are not limited to, the PROMOGRAN™ Matrix Wound Dressing and the PROMOGRAN PRISMA™ Matrix, commercially available from Acelity L.P. in San Antonio, Texas. The dressing may further include glutamine in an amount from about 0.1 grams to about 1 grams per gram of the collagen and ORC, as a nutrient; thus, the glutamine may be present in an amount in any embodiment herein from about 0.1 grams, about 0.2 grams, about 0.3 grams, about 0.4 grams, about 0.5 grams, about 0.6 grams, about 0.7 grams, about 0.8 grams, about 0.9 grams, about 1 gram (or any range including and/or in between any two of the preceding values) per gram of the combined collagen and ORC.

Cover

In any embodiment herein, the dressing may include and/or be used with one or more additional layers. For example, in any embodiment herein, such additional layers may perform any of a variety of functions including, but not limited to, adherence of the dressing to a tissue site or to surrounding tissues, increasing structural rigidity of the dressing, protection from moisture or other materials in the external environment, protection of a tissue site, delivery of one or more actives or other materials to the tissue site, or combinations of two or more thereof. In any embodiment herein, the additional layers may be conformable to a tissue site and/or to the surrounding tissues, for example, being capable of bending such that the tissue-facing surfaces of the dressing are in substantial contact with the tissue site and/or the surrounding tissues.

In any embodiment herein, the dressing may further include a cover. For example, as illustrated in an exemplary embodiment in FIG. 1, the dressing 100 is used with a cover 120, which may be positioned over the dressing 100 so as to enclose the dressing 100 at the tissue site. In any embodiment herein, the cover may have a wound-facing surface and an opposite back surface. For example, in any embodiment herein, the cover may support the dressing on the wound-facing surface of the cover such that a second surface of the dressing is proximate to the wound-facing surface of the cover. In any embodiment herein, the second surface of the dressing may be in contact with and adhered to the wound-facing surface of the cover.

In any embodiment herein, the cover may generally be configured to provide a bacterial barrier and protection from physical trauma. For example, the cover may be constructed from a material that can reduce evaporative losses and provide a fluid seal between two components or two environments, such as between a therapeutic environment and a local external environment. For example, in any embodiment herein, the cover may be an elastomeric film or membrane that can provide a seal at a tissue site for a given negative-pressure source. In any embodiment herein, the cover may have a high moisture-vapor transmission rate (MVTR). For example, in any embodiment herein, the MVTR may be at least 300 g/m$^2$ per twenty-four hours; thus, the MVTR may be about 300 g/m$^2$/24 hours, about 500 g/m$^2$/24 hours, about 750 g/m$^2$/24 hours, about 1000 g/m$^2$/24 hours, about 1500 g/m$^2$/24 hours, about 2000 g/m$^2$/24 hours, about 2500 g/m$^2$/24 hours, about 3000 g/m$^2$/24 hours, about 3500 g/m$^2$/24 hours, about 4000 g/m$^2$/24 hours, about 4500 g/m$^2$/24 hours, about 5000 g/m$^2$/24 hours, or any range including and/or in between any two of the preceding values. In any embodiment herein, the cover may be formed from a suitable polymer. For example, in any embodiment herein, the cover may include a polymer drape, such as a polyurethane film, that may be permeable to water vapor but generally impermeable to liquid. In any embodiment herein, the cover may have a thickness in the range of about from 25 to about 50 microns; thus, the thickness may include, but is not limited to, about 25 microns, about 30 microns, 35 microns, 40 microns, 45 microns, about 50 microns, or any range including and/or in between any two of the preceding values.

In any embodiment herein, the cover may be configured to be attached to an attachment surface, such as undamaged epidermis, a gasket, or another cover via an attachment device. For example, in any embodiment herein, the cover may be attached to tissue proximate a tissue site, such as epidermis, so as to form a sealed space. For example, in any embodiment, the attachment device may take any suitable form. In any embodiment herein, the attachment device may be a medically-acceptable, pressure-sensitive adhesive that extends about a periphery, a portion, or an entire surface of the cover. For example, in any embodiment herein, some or all of the cover may be coated with an adhesive, such as an acrylic adhesive, having a coating weight between 25-65 grams per square meter (g.s.m.). Thicker adhesives, or combinations of adhesives, may be applied in any embodiment herein, for example, to improve the seal and reduce leaks. Other example embodiments of an attachment device may include a double-sided tape, a paste, a hydrocolloid, a hydrogel, a silicone gel, or an organogel.

Secondary Layer

Additionally, in any embodiment herein, the dressing may further include a secondary layer. In any embodiment herein, the secondary layer may include fluid pathways interconnected so as to improve distribution or collection of fluids. For example, in any embodiment herein, the secondary layer may be a porous foam material having a plurality of interconnected cells or pores, for example, cellular foam, such as an open-cell foam, porous tissue collections, and other porous material such as gauze or felted mat generally include pores, edges, and/or walls adapted to form interconnected fluid pathways (e.g., channels). For example, in any embodiment herein, the secondary layer may be a foam having pore sizes in a range of 400-600 microns; thus, the secondary layer may be a foam in any embodiment herein having pore sizes of about 400 microns, about 420 microns, about 440 microns, about 460 microns, about 480 microns, about 500 microns, about 520 microns, about 540 microns, about 560 microns, about 580 microns, about 600 microns, or any range including and/or in between any two of the preceding values. Thus, in any embodiment herein, the secondary layer may be a reticulated polyurethane foam.

In any embodiment herein, the secondary layer may be characterized as exhibiting absorbency. For example, in any embodiment herein the secondary layer may exhibit an absorbency of at least 3 g saline/g, at least about 4 g saline/g, at least about 5 g saline/g, at least about 6 g saline/g, at least about 7 g saline/g, at least about 8 g saline/g, at least about 9 g saline/g, at least about 10 g saline/g, at least about 11 g saline/g, at least about 12 g saline/g, at least about 13 g saline/g, at least about 14 g saline/g, at least about 15 g saline/g, at least about 16 g saline/g, at least about 17 g saline/g, at least about 18 g saline/g, at least about 19 g saline/g, at least about 20 g saline/g, or any range including and/or in between any two of the preceding values. The secondary layer may be hydrophilic; for example, in any embodiment herein, the secondary layer may also absorb (e.g., wick) fluid away from a dressing. For example, in any embodiment herein, the wicking properties of the secondary layer may draw fluid away from dressing by capillary flow or other wicking mechanisms. In any embodiment herein, the secondary layer may be a hydrophilic foam such as a polyvinyl alcohol, open-cell foam. For example, in any embodiment herein, other hydrophilic foams may include, but are not limited to, hydrophilic foams made from polyether. Other foams that may exhibit hydrophilic characteristics include hydrophobic foams that have been treated or coated to provide hydrophilicity.

Negative-Pressure Therapy

The dressing of any embodiment described herein may be employed in a therapy in which a tissue site, for example, a wound, is treated with reduced pressure. Treatment of wounds or other tissue with reduced pressure may be commonly referred to as "negative-pressure therapy," but is also known by other names, including "negative-pressure wound therapy," "reduced-pressure therapy," "vacuum therapy," "vacuum-assisted closure," and "topical negative-pressure," for example. Negative-pressure therapy may provide a number of benefits, including migration of epithelial and subcutaneous tissues, improved blood flow, and microdeformation of tissue at a wound site. Together, these benefits may increase development of granulation tissue and reduce healing times.

Figure 2:
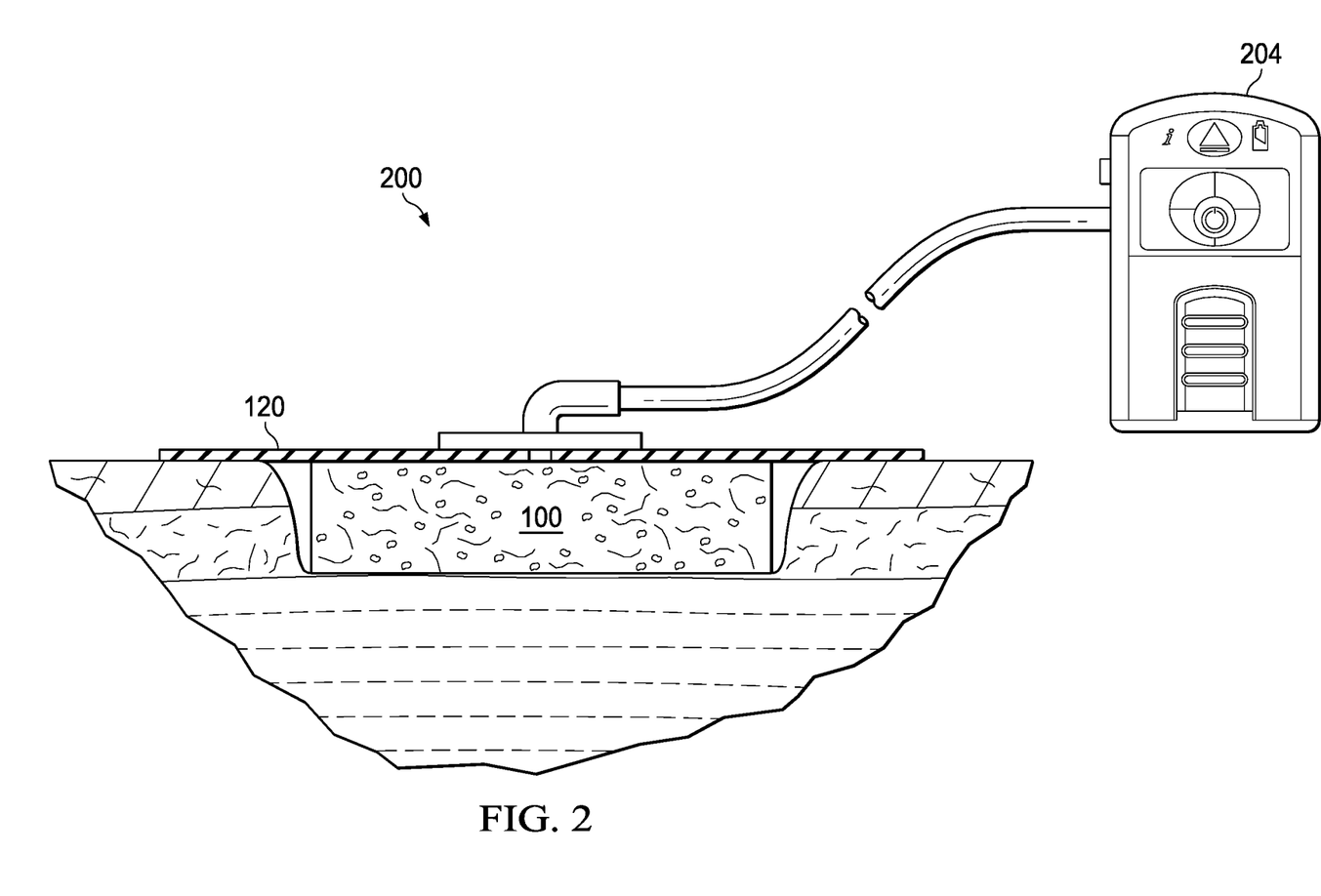
FIG. 2 is a simplified schematic diagram of an example embodiment of a negative pressure therapy system including the dressing of FIG. 1.

FIG. 2 illustrates an exemplary embodiment of a negative-pressure therapy system (200) in a simplified schematic. Generally, the negative-pressure therapy system may be configured to provide negative-pressure to a tissue site in accordance with this specification. In any embodiment herein, a negative-pressure therapy system may generally include a negative-pressure supply, and may include or be configured to be coupled to a distribution component. In general, a distribution component may refer to any complementary or ancillary component configured to be fluidly coupled to a negative-pressure supply in a fluid path between a negative-pressure supply and a tissue site. In the illustration provided in FIG. 2, the dressing 100 is an example of a distribution component fluidly coupled to a negative-pressure source 204 such that negative pressure may be applied to a tissue site via the dressing 100.

In any embodiment herein, the dressing may be generally configured to distribute negative pressure, to collect fluid, or both. The dressing may include or be configured as a manifold. A "manifold" in this context generally includes any composition or structure providing a plurality of pathways configured to collect or distribute fluid across a tissue site under pressure. For example, a manifold may be configured to receive negative pressure from the negative-pressure source and to distribute negative pressure through multiple apertures (e.g., pores), which may have the effect of collecting fluid and drawing the fluid toward the negative-pressure source. More particularly, as illustrated in FIG. 2, the dressing (100), for example, which may be configured to receive negative pressure from the negative-pressure source (204) and to distribute the negative pressure through the dressing (100), for example, which may have the effect of collecting fluid from a sealed space by drawing fluid from a tissue site through the dressing (100). Additionally or alternatively, the fluid path(s) may be reversed or a secondary fluid path may be provided to facilitate movement of fluid across a tissue site. Additionally or alternatively, the fluid pathways of a manifold may be interconnected to improve distribution or collection of fluids. Additionally or alternatively, a manifold may be a porous foam material having a plurality of interconnected cells or pores. For example, in any embodiment herein, open-cell foam may generally include pores, edges, and/or walls that may form interconnected fluid pathways (such as channels).

The fluid mechanics associated with using a negative-pressure source to reduce pressure in another component or location, such as within a sealed therapeutic environment, can be mathematically complex. However, the basic principles of fluid mechanics applicable to negative-pressure therapy are generally well-known to those skilled in the art. The process of reducing pressure may be described generally and illustratively herein as "delivering," "distributing," or "generating" negative pressure, for example.

In general, a fluid, such as wound fluid (for example, wound exudate and other fluids), flows toward lower pressure along a fluid path. Thus, the term "downstream" typically implies something in a fluid path relatively closer to a source of negative pressure or further away from a source of positive pressure. Conversely, the term "upstream" implies something relatively further away from a source of negative pressure or closer to a source of positive pressure. This orientation is generally presumed for purposes of describing various features and components herein. However, the fluid path may also be reversed in some applications (such as by substituting a positive-pressure source for a negative-pressure source) and this descriptive convention should not be construed as a limiting convention.

"Negative pressure" may generally refer to a pressure less than a local ambient pressure, such as the ambient pressure in a local environment external to a sealed therapeutic environment provided by the dressing. In many cases, the local ambient pressure may also be the atmospheric pressure proximate to or about a tissue site. Alternatively or additionally, the pressure may be less than a hydrostatic pressure associated with a tissue at a tissue site. While the amount and nature of negative pressure applied to a tissue site may vary according to therapeutic requirements, the pressure is generally a low vacuum, also commonly referred to as a rough vacuum, between −5 mm Hg (−667 Pa) and −500 mm Hg (−66.7 kPa). Common therapeutic ranges are between −50 mm Hg (−6.7 kPa) and −300 mm Hg (−39.9 kPa).

Additionally or alternatively, in any embodiment herein, a negative-pressure supply (such as the negative-pressure source 204, of FIG. 2) may be a reservoir of air at a negative pressure, or may be a manual or electrically-powered device that can reduce the pressure in a sealed volume, such as a vacuum pump, a suction pump, a wall suction port available at many healthcare facilities, or a micro-pump, for example. A negative-pressure supply may be housed within or used in conjunction with other components, such as sensors, processing units, alarm indicators, memory, databases, software, display devices, or user interfaces that further facilitate therapy. A negative-pressure source (e.g., negative-pressure source 204 of FIG. 2) may be combined with a controller and other components into a therapy unit. A negative-pressure supply may also have one or more supply ports configured to facilitate coupling and de-coupling of the negative-pressure supply to one or more distribution components.

In any embodiment herein, components may be fluidly coupled to each other to provide a path for transferring fluids (i.e., liquid and/or gas) between the components. For example, components may be fluidly coupled through a fluid conductor, such as a tube. As used herein, the term "fluid conductor" may include a tube, pipe, hose, conduit, or other structure with one or more lumina adapted to convey a fluid between two ends thereof. Typically, a fluid conductor may be an elongated, cylindrical structure with some flexibility, but the geometry and rigidity may vary. Additionally or alternatively, in any embodiment herein, the negative-pressure source may be operatively coupled to the dressing via a dressing interface. For example, and by way of reference to FIG. 2, dressing 100 may be coupled to negative-pressure source 204 via a dressing interface such that the dressing 100 receives negative pressure from the negative pressure source.

Methods

The present technology provides a method for preparing the dressing that may include forming a slurry including one or more bioresorbable components. For example, in any embodiment herein, the one or more bioresorbable components may include a structural protein and an oxidized cellulose in suitable amounts as described herein. In any embodiment herein, the slurry may include collagen and ORC. Additionally or alternatively, in any embodiment herein, the slurry may further include a metal (e.g., silver) in a suitable amount. In any embodiment herein, at least a portion of the metal may be present in a complex with a bioresorbable component, for example, an ORC-silver complex. Additionally or alternatively, in any embodiment herein, the methods may include adding one or more nutrients, as described herein in any embodiment (e.g., glutamine), to the slurry.

In any embodiment herein, the method may further include drying the slurry to form a sponge or a film. The drying may include freeze-drying the slurry, solvent-drying the slurry, or otherwise dehydrating the slurry. Freeze-drying may include freezing the slurry, followed by evaporating the solvent from the frozen slurry under reduced pressure. A method of freeze-drying may be similar to the method described for drying a collagen-based sponge in U.S. Pat. No. 2,157,224, which is incorporated by reference herein in its entirety. In any embodiment herein, the freeze-drying may be performed in one or more stages. Solvent-drying may include freezing the slurry, followed by immersing the slurry in a series of baths of a hygroscopic organic solvent (such as anhydrous isopropanol) to extract the water from the frozen slurry, followed by removing the organic solvent by evaporation. Methods of solvent drying are described, for example, in U.S. Pat. No. 3,157,524, which is incorporated herein by reference in its entirety. In any embodiment herein, the method may further include placing the slurry in a dehydration oven, which may evaporate water and/or solvent using suitably higher temperatures with or without circulation of air through a chamber containing a desiccant or the like.

In any embodiment herein, the method may further include treating the slurry, or the dried dressing, with a cross-linking agent such as epichlorohydrin, carbodiimide, hexamethylene diisocyanate (HMDI) orglutaraldehyde. Additionally or alternatively, cross-linking may be carried out dehydrothermally. In any embodiment herein, the particular method of cross-linking may be selected based upon a desired final product. For example, in any embodiment herein, HMDI may cross-link the primary amino groups of collagen, whereas carbodiimide may cross-link carbohydrate of the ORC to primary amino groups of the collagen.

In any embodiment herein, the method may further include applying one or more nutrients (e.g., glutamine) to the slurry and/or to the dried dressing. For example, in any embodiment herein, the nutrient may be applied to a slurry or dressing having a nutrient incorporated as a component of the slurry. Additionally or alternatively, in any embodiment herein, the nutrient may be applied to a slurry or dressing not having a nutrient incorporated as a component of the slurry. In any embodiment herein, the nutrient may be applied in any suitable form, for example, as a component of a nutrient solution. For example, in any embodiment herein, the solution that includes the nutrient may be prepared by mixing a suitable amount of the nutrient, for example, in powdered form or liquid form, with a solvent, such as water, to form the nutrient solution in a concentration such that the resultant dressing, after application of the nutrient solution, has the desired nutrient concentration.

The present technology also provides a therapy method, where the therapy method includes positioning the dressing with respect to the tissue site. For example, in operation, the dressing may be positioned proximate to the wound. The dressing may be used with any of a variety of wounds, such as those occurring from trauma, surgery or disease. For example, in any embodiment herein, such wounds may be chronic wounds venous ulcers, decubitus ulcers or diabetic ulcers. For example, the dressing may be placed within, over, on, or otherwise proximate to the tissue site. Additionally or alternatively, in any embodiment herein, a cover, (such as a cover 120 in FIG. 2), may be placed over the dressing and the cover sealed to an attachment surface near the tissue site. For example, the cover may be sealed to undamaged epidermis peripheral to a tissue site. In any embodiment herein, the dressing may be positioned first and, after the dressing has been positioned, the cover may be positioned. In any embodiment herein, the dressing and cover may be preassembled, for example, such that the dressing and cover are positioned with respect to each other prior to placement proximate the tissue site. Thus, the cover can provide a sealed therapeutic environment including the dressing and proximate to a tissue site, substantially isolated from the external environment.

In any embodiment herein, the dressing may be employed in the context of a negative-pressure therapy, where a negative-pressure therapy may further include fluidly coupling a negative-pressure source to the sealed space and operating the negative-pressure source to generate a negative pressure in the sealed space. For example, the negative-pressure source may be coupled to the dressing such that the negative-pressure source may be used to reduce the pressure in the sealed space. For example, negative pressure applied across the tissue site, for example, via the dressing may be effective to induce macrostrain and microstrain at the tissue site, as well as remove exudates and other fluids from the tissue site.

Advantages

The present technology provides significant advantages, for example, when used in the context of a therapy.

For example, when the dressings and systems are used in a therapy, the dressings and systems may advantageously modulate protease activity. For example, when the dressings and systems are used in a therapy, wound fluid (e.g., wound exudate) may come into contact with the dressings. Upon contact between the wound fluid and the dressings, the dressing may degrade and, as the bioresorbable structure degrades, for example, as the ORC degrades, glucuronic acid may be released, which may have the effect of lowering pH. Without wishing to be bound by theory, a low pH is thought to help to inhibit bacterial growth. Additionally, ORC may help to stimulate growth, for example, by modulating protease activity. For example, ORC may be effective to modulate the activity of destructive enzymes such as elastase and matrix metalloproteinase (MMP). Enzymes, such as proteases, may be destructive or detrimental to wound healing, particularly, when an over-abundance of such proteases are present at a tissue site (e.g., at a wound). As such, in some embodiments, the capability to use the bioresorbable layers, dressings, and systems to modulate the activity of such enzymes, such as proteases, may be beneficial to wound healing.

Additionally, when the dressings and systems are used in a therapy, the dressings and systems may advantageously improve wound chronicity. For example, and again not intending to be bound by theory, insufficient nutrition during wound healing may impair or delay the wound healing process. For example, increased nutritional requirements associated with wound healing may be the result of increased protein synthesis and immune responses as may occur during wound healing. Moreover, because the vasculature surrounding wounds is often poor, nutrients may be unable to efficiently reach the tissue site. The provision of glutamine and other nutrients proximate to a wound, such as by the dressings and systems may help to significantly improve wound healing by providing necessary nutrients proximate to the wound.

The examples herein are provided to illustrate advantages and benefits of the present technology and to further assist a person of ordinary skill in the art with preparing or using the dressings of the present technology. The examples herein are also presented in order to more fully illustrate the preferred aspects of the present technology. The examples should in no way be construed as limiting the scope of the present technology, as defined by the appended claims. The examples can include or incorporate any of the variations, aspects or embodiments of the present technology described above. The variations, aspects or embodiments described above may also further each include or incorporate the variations of any or all other variations, aspects or embodiments of the present technology.

EXAMPLES

Figure 3:
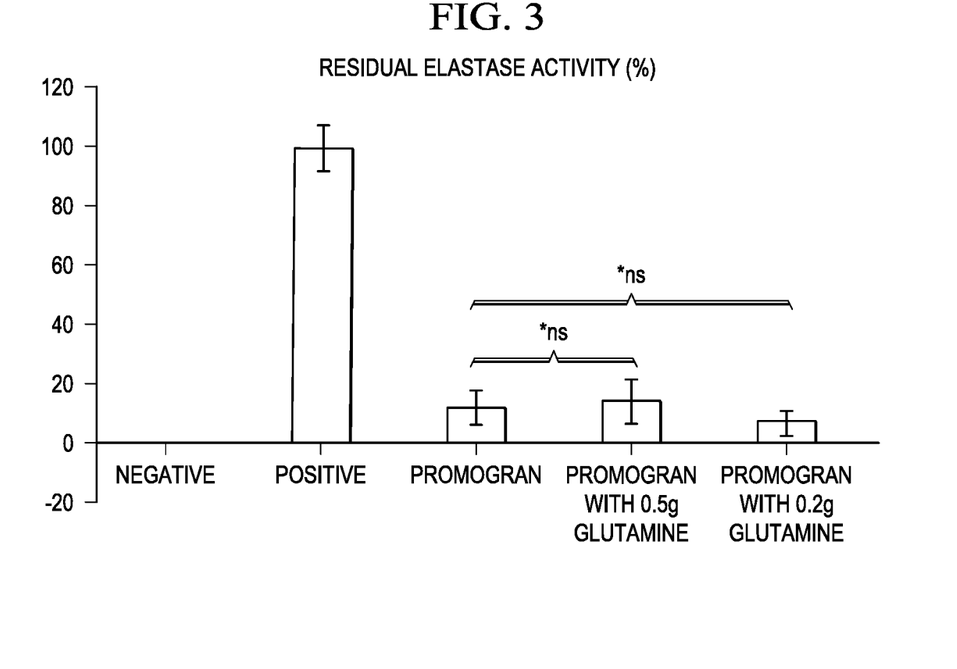
FIG. 3 is a diagrammatic illustration of the effect of a nutrient upon the protease-modulating activity of collagen and ORC.

Referring to FIG. 3, the effect of a nutrient upon the protease-modulating activity of a collagen/ORC layer is illustrated. In FIG. 3, residual elastase activity is shown for a negative control, a positive control, a dressing comprising collagen and ORC (e.g., the PROMOGRAN™ Matrix Wound Dressing), a dressing comprising collagen, ORC and 0.5 grams per gram of the dressing of glutamine, and a dressing comprising collagen, ORC and 0.2 grams per gram of the dressing of glutamine. The data in FIG. 3 demonstrates that the addition of glutamine to a collagen/ORC dressing does not significantly diminish the protease-modulating activity of the dressing, particularly, the elastase-modulating activity of that bioresorbable layer.

Figure 4:
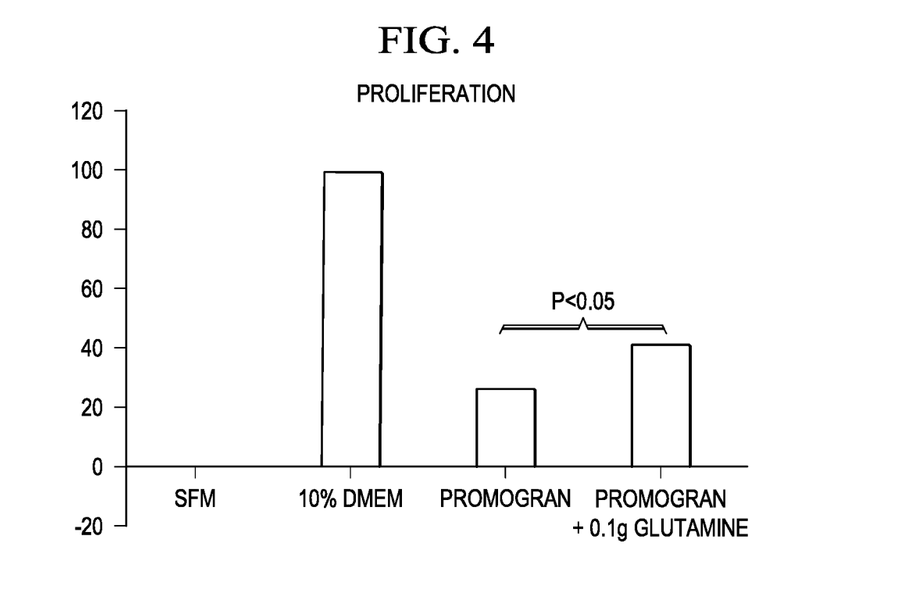
FIG. 4 is a diagrammatic illustration of the effect of a nutrient upon cellular proliferation.

Referring to FIG. 4, the effect of a nutrient upon cellular proliferation is illustrated. In FIG. 4, the proliferation of human dermal fibroblast cells is shown for a composition comprising 10% Dulbecco's Modified Eagle's Medium, a composition comprising collagen and ORC, and a composition comprising collagen, ORC and 0.1 grams per gram of the composition of glutamine. The data in FIG. 4 demonstrates that the addition of glutamine to such a composition, for example, a bioresorbable layer, yields a significant improvement in the proliferation of human dermal fibroblasts compared with the collagen and ORC bioresorbable layer.

EQUIVALENTS

While certain embodiments have been illustrated and described, a person with ordinary skill in the art, after reading the foregoing specification, can effect changes, substitutions of equivalents and other types of alterations to the compounds of the present technology or salts, pharmaceutical compositions, derivatives, prodrugs, metabolites, tautomers or racemic mixtures thereof as set forth herein. Each aspect and embodiment described above can also have included or incorporated therewith such variations or aspects as disclosed in regard to any or all of the other aspects and embodiments.

The present technology is also not to be limited in terms of the particular aspects described herein, which are intended as single illustrations of individual aspects of the present technology. Many modifications and variations of this present technology can be made without departing from its spirit and scope, as will be apparent to those skilled in the art. Functionally equivalent methods within the scope of the present technology, in addition to those enumerated herein, will be apparent to those skilled in the art from the foregoing descriptions. Such modifications and variations are intended to fall within the scope of the appended claims. It is to be understood that this present technology is not limited to particular methods, reagents, compounds, compositions, labeled compounds or biological systems, which can, of course, vary. It is also to be understood that the terminology used herein is for the purpose of describing particular aspects only, and is not intended to be limiting. Thus, it is intended that the specification be considered as exemplary only with the breadth, scope and spirit of the present technology indicated only by the appended claims, definitions therein and any equivalents thereof.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

In addition, where features or aspects of the disclosure are described in terms of Markush groups, those skilled in the art will recognize that the disclosure is also thereby described in terms of any individual member or subgroup of members of the Markush group. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents (for example, journals, articles and/or textbooks) referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

The present technology may include, but is not limited to, the features and combinations of features recited in the following lettered paragraphs, it being understood that the following paragraphs should not be interpreted as limiting the scope of the claims as appended hereto or mandating that all such features must necessarily be included in such A. A dressing configured to be positioned adjacent to a tissue site, the dressing comprising:
  oxidized regenerated cellulose (ORC);
  collagen; and
  at least one nutrient comprising glutamine.
B. The dressing of Paragraph A, wherein the dressing comprises from about 50% to about 60% collagen by weight of the dressing.
C. The dressing of Paragraph A or Paragraph B, wherein the dressing comprises from about 40% to about 50% ORC by weight of the dressing.
D. The dressing of any one of Paragraphs A-C, wherein the dressing comprises from about 0.1 grams of glutamine per gram of the ORC and the collagen to about 1 gram of glutamine per gram of the ORC and the collagen.
E. The dressing of any one of Paragraphs A-D, further comprising an antimicrobial agent.
F. The dressing of Paragraph E, wherein the antimicrobial agent comprises silver.
G. The dressing of Paragraph F, wherein the silver is complexed with the ORC.
H. The dressing of any one of Paragraphs A-G, wherein the dressing comprises a sponge.
I. The dressing of any one of Paragraphs A-H, wherein the dressing comprises a first surface, a second surface opposite the first surface, and a thickness, wherein the glutamine is applied to the dressing such that at least about 90% of the glutamine by weight is within about 50% of the thickness of the first surface.
J. The dressing of Paragraph I, wherein the glutamine is applied to the wound dressing such that at least about 99% of the glutamine by weight is within about 50% of the thickness of the first surface.
K. The dressing of any one of Paragraphs A-G, wherein the dressing is formed from a composition comprising the ORC, the collagen, and the glutamine.
L. The dressing of any one of Paragraphs A-G, wherein the dressing comprises a first surface, a second surface opposite the first surface, a thickness, and a film applied to the first surface, wherein the film comprises the glutamine.
M. The dressing of any one of Paragraphs A-L, wherein the at least one nutrient further comprises a vitamin.
N. The dressing of any one of Paragraphs A-M, further comprising a wound healing agent.
O. The dressing of Paragraph N, wherein the wound healing agent comprises a non-steroidal anti-inflammatory drug, a steroid, an anti-inflammatory cytokine, an anaesthetic, an antimicrobial agent, a growth factor, or combinations thereof.
P. The dressing of Paragraph O, wherein the growth factor is selected from the group consisting of a platelet-derived growth factor (PDGF), a fibroblast growth factor (FGF), an epidermal growth factor (EGF), and combinations thereof.
Q. The dressing of any one of Paragraphs A-P, wherein the at least one nutrient further comprises an amino acid other than glutamine.
R. The dressing of any one of claims A-Q, wherein at least a portion of the dressing is freeze dried.
S. The dressing of any one of Paragraphs A-R, further comprising a cover configured to be placed over a bioresorbable layer comprising the ORC and the collagen so as to form a sealed space including the tissue site.
T. A method for providing therapy to a tissue site, the method comprising:
  positioning a dressing adjacent to the tissue site, the dressing comprising oxidized regenerated cellulose (ORC), collagen, and at least one nutrient comprising glutamine.
U. The method of Paragraph T, wherein the dressing comprises from about 50% to about 60% collagen by weight of the dressing.
V The method of Paragraph T or Paragraph U, wherein the dressing comprises from about 40% to about 50% ORC by weight of the dressing.
W. The method of any one of Paragraphs T-V, wherein the dressing comprises from about 0.1 grams of glutamine per gram of the ORC and the collagen to about 1 gram of glutamine per gram of the ORC and the collagen.
X. The method of any one of Paragraphs T-W, wherein the dressing further comprises an antimicrobial agent.
Y. The method of Paragraph X, wherein the antimicrobial agent comprises silver.
Z. The method of Paragraph Z, wherein the silver is complexed with the ORC.
AA. The method of any one of Paragraphs T-Z, wherein the dressing comprises a sponge.
AB. The method of Paragraph AA, wherein the dressing comprises a first surface, a second surface opposite the first surface, and a thickness, wherein the glutamine is applied to the dressing such that at least about 90% of the glutamine by weight is within about 50% of the thickness of the first surface.
AC. The method of Paragraph AB, wherein the glutamine is applied to the wound dressing such that at least about 99% of the glutamine by weight is within about 50% of the thickness of the first surface.
AD. The method of any one of Paragraphs T-Z, wherein the dressing is formed from a composition comprising the ORD, the collagen, and the glutamine.
AE. The method of any one of Paragraphs T-Z, wherein the dressing comprises a first surface, a second surface opposite the first surface, a thickness, and a film applied to the first surface, wherein the film comprises the glutamine.
AF. The method of any one of Paragraphs T-AE, wherein the at least one nutrient further comprises a vitamin.
AG. The method of any one of Paragraphs T-AF, wherein the dressing further comprises a wound healing agent.
AH. The method of claim AG, wherein the wound healing agent comprises a non-steroidal anti-inflammatory drug, a steroid, an anti-inflammatory cytokine, an anaesthetic, an antimicrobial agent, a growth factor, or combinations thereof.

AI. The method of Paragraph AH, wherein the growth factor is selected from the group consisting of a platelet-derived growth factor (PDGF), a fibroblast growth factor (FGF), an epidermal growth factor (EGF), or combinations thereof.

AJ. The method of any one of Paragraphs T-AI, wherein the at least one nutrient further comprises an amino acid other than glutamine.

AK. The method of any one of Paragraphs T-AJ, wherein at least a portion of the dressing is freeze dried.

AL. The method of any one of Paragraphs T-AK, further comprising sealing the dressing to tissue surrounding the tissue site to form a sealed space.

AM. The method of any one of Paragraphs T-AL, wherein the dressing further comprises a cover configured to be placed over a bioresorbable layer comprising the ORC and the collagen so as to form the sealed space.

AN. The method of Paragraph AM, wherein sealing the dressing to the tissue surrounding the tissue site comprises sealing the cover to the tissue surrounding the tissue site.

AO. The method of any one of Paragraphs AL-AN, further comprising:
fluidly coupling a negative-pressure source to the sealed space; and
operating the negative-pressure source to generate a negative pressure within the sealed space.

Other embodiments are set forth in the following claims, along with the full scope of equivalents to which such claims are entitled.

What is claimed is:

1. A dressing configured to be positioned in contact with a wound, the dressing comprising:
   oxidized regenerated cellulose (ORC), the ORC being present in the dressing in an effective amount to modulate protease activity in the wound when the dressing is in contact with the wound;
   collagen; and
   at least one nutrient comprising glutamine,
   wherein the dressing is bioresorbable,
   wherein the glutamine is configured to be released to the wound when the dressing is positioned in contact with the wound, and
   wherein the glutamine is present in the dressing in an effective amount to improve proliferation of human dermal fibroblasts in the wound when the dressing is in contact with the wound without diminishing the protease modulating activity of the ORC.

2. The dressing of claim 1, wherein the dressing comprises from about 50% to about 60% collagen by weight of the dressing.

3. The dressing of claim 1, wherein the dressing comprises from about 40% to about 50% ORC by weight of the dressing.

4. The dressing of claim 1, wherein the dressing comprises from about 0.1 grams of glutamine per gram of the ORC and the collagen to about 0.2 grams of glutamine per gram of the ORC and the collagen.

5. The dressing of claim 1, further comprising an antimicrobial agent.

6. The dressing of claim 5, wherein the antimicrobial agent comprises silver.

7. The dressing of claim 6, wherein the silver is complexed with the ORC.

8. The dressing of claim 1, wherein the dressing comprises a sponge.

9. The dressing of claim 1, wherein the dressing comprises a first surface configured to contact the wound, a second surface opposite the first surface, and a thickness, and wherein the glutamine is applied to the first surface of the dressing such that at least about 90% of the glutamine by weight is within about 50% of the thickness nearest the first surface, and wherein the glutamine is applied to the first surface of the dressing in an effective amount to promote wound healing when the first surface of the dressing is positioned in contact with the wound.

10. The dressing of claim 9, wherein the glutamine is applied to the first surface of the dressing such that at least about 99% of the glutamine by weight is within about 50% of the thickness nearest the first surface.

11. The dressing of claim 1, wherein the dressing is formed from a composition comprising the ORC, the collagen, and the glutamine, and wherein the glutamine is applied to the first surface of the dressing in an effective amount to promote wound healing when the first surface of the dressing is positioned in contact with the wound.

12. The dressing of claim 1, wherein the dressing comprises a first surface, a second surface opposite the first surface, a thickness, and a film applied to the first surface, wherein the film comprises the glutamine, and wherein the glutamine is present in the film in an effective amount to promote wound healing when the dressing is positioned in contact with the wound.

13. The dressing of claim 1, wherein the at least one nutrient further comprises a vitamin.

14. The dressing of claim 1, further comprising a wound healing agent.

15. The dressing of claim 14, wherein the wound healing agent comprises a non-steroidal anti-inflammatory drug, a steroid, an anti-inflammatory cytokine, an anaesthetic, an antimicrobial agent, a growth factor, or combinations thereof.

16. The dressing of claim 15, wherein the wound healing agent comprises the growth factor, which is selected from the group consisting of a platelet-derived growth factor (PDGF), a fibroblast growth factor (FGF), an epidermal growth factor (EGF), and combinations thereof.

17. The dressing of claim 1, wherein the at least one nutrient further comprises an amino acid other than glutamine.

18. The dressing of claim 1, wherein at least a portion of the dressing is freeze dried.

19. The dressing of claim 1, further comprising a cover configured to be placed over a bioresorbable layer comprising the ORC and the collagen so as to form a sealed space including the tissue site.

20. The dressing of claim 1, wherein the at least one nutrient further comprises a fatty acid.

21. The dressing of claim 20, wherein the fatty acid comprises alpha-linolenic acid, linoleic acid, or a combination thereof.

22. A method for providing therapy to a wound, the method comprising:
    positioning a dressing comprising oxidized regenerated cellulose ORC); collagen; and
        at least one nutrient comprising glutamine in contact with the wound,
    wherein the ORC and collagen are bioresorbable,
    wherein the glutamine is configured to be released to the wound when the dressing is positioned in contact with the wound, wherein the ORC is present in the dressing in an effective amount to modulate protease activity in the wound when the dressing is in contact with the wound, and wherein the glutamine is present in the dressing in an effective amount to improve proliferation of human dermal fibroblasts in the wound when the dressing is in contact with the wound without diminishing the protease modulating activity of the ORC.

23. A dressing configured to be positioned in contact with a wound, the dressing comprising:

about 40% to about 50% oxidized regenerated cellulose (ORC) by weight of the dressing, the ORC being bioresorbable and being present in the dressing in an effective amount to modulate protease activity in the wound when the dressing is in contact with the wound;

about 50% to about 60% collagen by weight of the dressing, the collagen being bioresorbable; and at least one nutrient comprising glutamine configured to be released to the wound when the dressing is positioned in contact with the wound, the glutamine being present in the dressing in an amount of from about 0.1 grams per gram of the ORC and the collagen to about 0.2 grams per gram of the ORC and the collagen, wherein the glutamine is present in the dressing in an effective amount to improve proliferation of human dermal fibroblasts in the wound when the dressing is in contact with the wound without diminishing the protease modulating activity of the ORC.

* * * * *